(12) United States Patent
Hall et al.

(10) Patent No.: US 7,842,188 B2
(45) Date of Patent: *Nov. 30, 2010

(54) METHOD FOR REMOVAL OF GUANIDINE COMPOUND FROM AQUEOUS MEDIA

(75) Inventors: David Bruce Hall, Ballston Lake, NY (US); Thomas Link Guggenheim, Mt. Vernon, IN (US); James Manio Silva, Clifton Park, NY (US); Farid Fouad Khouri, Clifton Park, NY (US); Matthew Hal Littlejohn, Green Island, NY (US); Balakrishnan Ganesan, Bangalore (IN); Ashok Shankrappa Shyadligeri, Bangalore (IN); Pradeep Jeevaji Nadkarni, Bangalore (IN)

(73) Assignee: Sabic Innovative Plastics IP B.V., Pittsfield, MA (US)

( * ) Notice: Subject to any disclaimer, the term of this patent is extended or adjusted under 35 U.S.C. 154(b) by 205 days.

This patent is subject to a terminal disclaimer.

(21) Appl. No.: 11/684,882

(22) Filed: Mar. 12, 2007

(65) Prior Publication Data
US 2007/0161821 A1    Jul. 12, 2007

Related U.S. Application Data

(63) Continuation-in-part of application No. 10/743,239, filed on Dec. 22, 2003.

(51) Int. Cl.
*B01D 61/00* (2006.01)
*B01D 63/00* (2006.01)
(52) U.S. Cl. .................... 210/652; 210/651; 210/653
(58) Field of Classification Search .................. 210/650, 210/634, 651, 652, 663, 653; 528/449, 125, 528/149, 491, 170
See application file for complete search history.

(56) References Cited

U.S. PATENT DOCUMENTS

| 3,952,057 | A | 4/1976 | Schmidt et al. |
| 4,040,990 | A | 8/1977 | Neely |
| 4,157,348 | A | 6/1979 | Ono et al. |
| 4,297,220 | A | 10/1981 | Meitzner et al. |
| 4,729,834 | A | 3/1988 | Itoh et al. |
| 4,839,331 | A | 6/1989 | Maroldo et al. |
| 4,914,235 | A | 4/1990 | Grambow et al. |
| 4,957,897 | A | 9/1990 | Maroldo et al. |
| 5,041,662 | A | 8/1991 | Grambow et al. |
| 5,081,298 | A | 1/1992 | Brunelle |
| 5,094,754 | A | 3/1992 | Maroldo et al. |
| 5,104,530 | A | 4/1992 | Maroldo et al. |
| 5,116,975 | A | 5/1992 | Brunelle |
| 5,132,423 | A | 7/1992 | Brunelle |
| 5,229,482 | A | 7/1993 | Brunelle |
| 5,530,052 | A | 6/1996 | Takekoshi et al. |
| 5,696,290 | A | 12/1997 | Ruettimann et al. |
| 5,759,406 | A | 6/1998 | Phelps et al. |
| 5,830,974 | A | 11/1998 | Schmidhauser et al. |
| 5,892,294 | A | 4/1999 | Reid |
| 6,214,235 | B1 | 4/2001 | Silva |
| 6,235,934 | B1 * | 5/2001 | Caringi et al. ............. 564/241 |
| 6,570,038 | B1 | 5/2003 | Caringi et al. |
| 6,630,568 | B1 | 10/2003 | Johnson et al. |
| 6,790,934 | B2 * | 9/2004 | Johnson et al. ............. 528/499 |
| 2004/0115169 | A1 | 6/2004 | Wolfe et al. |
| 2005/0066118 | A1 | 3/2005 | Perry et al. |

FOREIGN PATENT DOCUMENTS

JP    03080934    4/1991

OTHER PUBLICATIONS

Willi Kantlehner et al., "Herstellung von 1,1,2,3,3-Pentasubstituierten und 1,1,2,2,3,3,-Hexasubstituierten Guanidiniumsalzen Sowie von 1,1,2,3,3-Pentaalkylguanidinen", Liebigs Ann. Chem., pp. 108-126, 1984.
Przemyslaw Pruszynski, "Synthesis and Properties of Phenyl Substituted Derivatives of 2-Phenyl-1,1,3,3-Tetramethylguanidine", Department of Chemistry, Adam Mickiewicz University, 60-780 Poznan, Poland, Can. J. Chem., vol. 65, pp. 626-629, 1987.

* cited by examiner

*Primary Examiner*—Ana M Fortuna

(57) ABSTRACT

Disclosed is a method for removing a neutral or an ionic guanidine compound from aqueous media optionally comprising an alkali metal halide, wherein the method is selected from the group consisting of (a) adsorption onto a carbonaceous adsorbent, (b) adsorption onto a clay adsorbent, (c) filtration through a nanofiltration membrane, and (d) removal of water and calcination.

14 Claims, No Drawings

METHOD FOR REMOVAL OF GUANIDINE COMPOUND FROM AQUEOUS MEDIA

CROSS REFERENCE TO RELATED APPLICATION

This application is a continuation-in-part application of U.S. patent application Ser. No. 10/743,239, filed Dec. 22, 2003 now published U.S. Patent Application No. 2005/0029194.

BACKGROUND OF THE INVENTION

The present invention relates a method for removing a guanidine compound from aqueous media. More particularly, it relates a method for removing an ionic or a neutral, or both an ionic and a neutral guanidine compound from aqueous media.

Guanidine compounds are frequently used as catalysts in chemical reactions, for example because of their basic properties in the case of neutral guanidine compounds or because of their phase transfer catalytic properties in the case of ionic guanidine compounds (also know as guanidinium salts). In particular examples U.S. Pat. No. 5,229,482 discloses a displacement method for the preparation of polyetherimides from bis(chlorophthalimides) and alkali metal salts of dihydroxy-substituted aromatic hydrocarbons using a solvent of low polarity such as o-dichlorobenzene in the presence of a thermally stable phase transfer catalyst such as a hexaalkylguanidinium halide. U.S. Pat. No. 5,830,974 discloses a similar method using a monoalkoxybenzene such as anisole as solvent. Isolation of product from organic media comprising a guanidine compound often involves washing the organic media with water. In these cases all or at least a portion of guanidine compound may transfer to the aqueous phase. For proper disposal of the wash water and for recovery and reuse of valuable guanidine compounds, a method is needed to remove a guanidine compound from the aqueous media.

U.S. Pat. No. 5,759,406 teaches removal of adsorbates such as guanidinium salts from brine solution using a non-ion-exchangeable adsorbent polymeric resin. However, the polymeric resins show limited adsorption capacity and must be used in relatively large amounts for efficient removal of the target adsorbates.

U.S. Pat. No. 6,214,235 teaches purification of brine solution for electrolysis by removal of organic salts using carbonaceous adsorbents. However, the method requires brine solutions with concentration of salt greater than 5 weight percent and makes no suggestion for recovery of organic salts. There is a continuing need for a method to remove guanidine compounds from aqueous media, particularly for wastewater treatment and disposal, and for recovery of guanidine compounds for further use.

BRIEF DESCRIPTION OF THE INVENTION

The present inventors have discovered a method for removing guanidine compounds from aqueous media. The method is efficient and is also applicable to a wide variety of aqueous media. In one embodiment the method works surprisingly well for removing a guanidine compound from aqueous media quite low in ionic strength as measured by concentration of salt.

In one of its embodiments the present invention comprises a method for removing a neutral or an ionic guanidine compound from an aqueous media comprising less than 4 wt. % of an alkali metal halide, wherein the method is selected from the group consisting of (a) adsorption onto a carbonaceous adsorbent, (b) adsorption onto a clay adsorbent, (c) filtration through a nanofiltration membrane, and (d) removal of water and calcination.

In another of its embodiments the present invention comprises a method for removing a guanidine compound selected from the group consisting of hexaethylguanidinium chloride, pentaethylguanidine, and mixtures thereof, from an aqueous media optionally comprising an alkali metal halide, wherein the method is selected from the group consisting of (b) adsorption onto a clay adsorbent, (c) filtration through a nanofiltration membrane having a molecular weight cut-off sufficient to retain from about 80% to about 100% of the guanidine compound, and (d) removal of water and calcination at a temperature in a range of between about 500° C. and about 600° C.; wherein the concentration of guanidine compound present initially in the aqueous media ranges from about 1 part per million to about 20,000 parts per million, and wherein the concentration of guanidine compound following removal is less than 20% of the initial concentration.

Various other features, aspects, and advantages of the present invention will become more apparent with reference to the following description, examples, and appended claims.

DETAILED DESCRIPTION OF THE INVENTION

In the following specification and the claims which follow, reference will be made to a number of terms which shall be defined to have the following meanings. The singular forms "a", "an" and "the" include plural referents unless the context clearly dictates otherwise. "Optional" or "optionally" means that the subsequently described event or circumstance may or may not occur, and that the description includes instances where the event occurs and instances where it does not. The phrase "wastewater" is sometimes used to refer to aqueous media comprising at least one guanidine compound. However, it should be understood that the present invention encompasses methods to treat any aqueous media comprising at least one guanidine compound.

The term "guanidine compound" as used in the present invention describes a composition comprising either an ionic guanidinium salt or a neutral guanidine compound, or both. In one embodiment guanidine compounds comprise ionic guanidinium species of the formula (I):

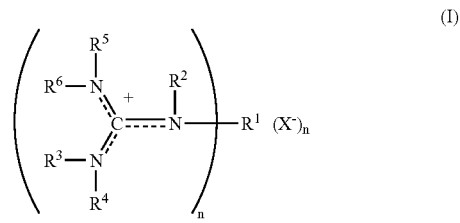

wherein each of $R^2$, $R^3$, $R^4$, $R^5$ and $R^6$ is independently a primary alkyl radical and $R^1$ a primary alkyl or bis(primary alkylene) radical, or at least one of $R^2$, $R^3$, $R^4$, $R^5$ and $R^6$ is hydrogen, or at least one of the $R^1$-$R^2$, $R^3$-$R^4$ or $R^5$-$R^6$ combinations with the connecting nitrogen atom forms a heterocyclic radical; the moiety X is an anion; and the value of the parameter n is 1 or 2. The moiety X in formula (I) may be any anion and is preferably an anion of a strong acid, illustrative examples of which comprise chloride, bromide and methanesulfonate. Chloride and bromide ions are usually preferred.

The value of n will be 1 or 2 depending upon whether $R^1$ is alkyl or alkylene, respectively.

In another embodiment guanidine compounds comprise neutral species of the formula (II):

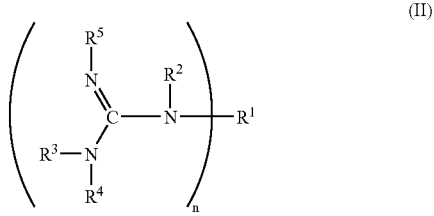

(II)

wherein each of $R^2$, $R^3$, $R^4$ and $R^5$ is independently a primary alkyl radical and $R^1$ is a primary alkyl or bis(primary alkylene) radical, or at least one of the $R^1$-$R^2$ or $R^3$-$R^4$ combinations with the connecting nitrogen atom forms a heterocyclic radical; and the value of the parameter n is 1 or 2.

The alkyl radicals suitable as $R^{1-6}$ in formulas (I) and (II) comprise primary alkyl radicals, generally containing about 1-12 carbon atoms. $R^1$ is usually an alkyl radical of the same structure or a $C_{2-12}$ alkylene radical in which the terminal carbons are primary; most preferably, it is $C_{2-6}$ alkyl or $C_{4-8}$ straight chain alkylene. Alternatively, any combination of $R^{1-6}$ and the corresponding nitrogen atom(s) may form a heterocyclic radical including, but not limited to, piperidino, pyrrolo or morpholino.

As indicated by the dotted bonds in formula (I), the positive charge in the guanidinium salt is delocalized over one carbon and three nitrogen atoms. This is believed to contribute to the salts stability under the relatively high temperature conditions encountered by the salts in some applications. As a result, decomposition of the guanidinium salt does not occur or occurs only to a very minor extent. The results include suppression of by-product formation and potential for continued use of the salts via recycle.

Guanidinium salts include those disclosed in U.S. Pat. Nos. 5,116,975, 5,132,423 and 5,229,482. Hexaalkylguanidinium salts may be prepared by the reaction of a corresponding urea (e.g., a tetraalkylurea) with phosgene or phosphorus oxychloride, or by the reaction of a similar thiourea with an N,N-dialkylcarbamoyl halide, to yield a chloroformamidinium salt, frequently referred to as a "Vilsmeier salt", followed by reaction of said salt with a corresponding amine (e.g., a dialkylamine). Reference is made to Kantlehner et al., Liebigs Ann. Chem., 1984, pp. 108-126, and Pruszynski, Can. J. Chem., vol. 65, pp. 626-629 (1987). α,ω-Bis(pentaalkylguanidinium)alkane salts may be similarly prepared by reaction of the chloroformamidinium salt with a monoalkylamine, followed by reaction of the resulting pentaalkylguanidinium salt with an alkylene dihalide. The (alpha, omega)-bis(pentaalkylguanidinium)alkane salts defined when $R^1$ is alkylene and n is 2 are disclosed, for example, in U.S. Pat. No. 5,081,298.

The concentration of guanidine compound initially in aqueous media ranges from about 0.5 parts per million (ppm) to 100,000 ppm (10%), by weight of the aqueous media, and preferably ranges from about 1 ppm to about 20,000 ppm (2%) by weight of the aqueous media. In particularly preferred embodiments the concentration of guanidine compound initially in aqueous media ranges from about 1 ppm to about 1000 ppm, or from about 1 ppm to about 500 ppm.

Aqueous media in the present invention comprises any aqueous media comprising at least 90 percent by weight water and at least one ionic or neutral guanidine compound, or both of at least one ionic and at least one neutral guanidine compound. Aqueous media are defined herein as comprising at least 90 percent by weight water. In various embodiments aqueous media may also comprise any additional components which are water-soluble or at least partially water-soluble and which arise from or are present initially in chemical reactions in which a guanidine compound is present in the capacity of reaction product, reaction byproduct, decomposition product, reactant or catalyst, or in more than one capacity. In some particular embodiments aqueous media comprises at least one guanidine compound which was added as a catalyst in a displacement reaction, illustrative examples of which include polymerization reactions. In one particular embodiment aqueous media comprises both at least one guanidine compound added as a catalyst in a polymerization reaction and at least one guanidine compound decomposition product derived from an initial guanidine compound.

Guanidine compounds which may be employed as catalysts in displacement reactions comprise guanidinium salts, illustrative examples of which include hexaalkylguanidinium salts and alpha, omega-bis(pentaalkylguanidinium)alkane salts. In particular embodiments hexaalkylguanidinium salts and alpha, omega-bis(pentaalkylguanidinium)alkane salts comprise halogen salts, particularly bromides and chlorides. In one particular embodiment a hexaalkylguanidinium salt employed as a catalyst is hexaethylguanidinium chloride. In another particular embodiment an alpha,omega-bis(pentaalkylguanidinium)alkane salt employed as a catalyst is 1,6-bis(penta-n-butylguanidinium)hexane dibromide. In other particular embodiments guanidinium salts are employed as catalysts in displacement reactions of bisphenol salts such as bisphenol A disodium salt with nitro- or halo-substituted imides such as 4-nitro-N-methylphthalimide, 4-chloro-N-methylphthalimide or 1,3-bis(N-(4-chlorophthalimido))benzene also known as 2,2'-(1,3-phenylene)bis(5-chloro-1H-isoindole-1,3(2H-dione)), to produce bisimides or polyetherimides. In particular examples U.S. Pat. No. 5,229,482 discloses a displacement method for the preparation of polyetherimides from bis(chlorophthalimides) and alkali metal salts of dihydroxy-substituted aromatic hydrocarbons using a solvent of low polarity such as o-dichlorobenzene in the presence of a thermally stable phase transfer catalyst such as a hexaalkylguanidinium halide. U.S. Pat. No. 5,830,974 discloses a similar method using a monoalkoxybenzene such as anisole as solvent.

In some embodiments an aqueous medium comprising at least one guanidine compound is formed when a reaction mixture comprising an organic solvent and at least one guanidine compound is washed with water. Thus, in some embodiments an aqueous medium comprising at least one guanidine compound may optionally comprise less than about 5 wt. % of an organic solvent and any other water-soluble or partially water-soluble species present in said reaction mixture. In various embodiments said organic solvent has a boiling point above about 150° C. and includes as illustrative examples ortho-dichlorobenzene, para-dichlorobenzene, dichlorotoluene, 1,2,4-trichlorobenzene, diphenyl sulfone, phenetole, anisole and veratrole, and mixtures thereof. In some embodiments said organic solvent forms an azeotrope with water.

In certain types of reactions such as displacement reactions a salt by-product such as an alkali metal salt may be formed as a side-product. Thus, in some embodiments an aqueous medium comprising at least one guanidine compound may optionally comprise an alkali metal salt, and in particular, sodium chloride or potassium chloride. When an alkali metal salt is present in the aqueous media, it is typically present at a level in a range of between about 0.01 wt. % and about 10 wt. %, based on the total weight of the aqueous media. In other embodiments when an alkali metal salt is present in the aqueous media, it is typically present at less than 5 wt. %, or less than 4 wt. %, or less than 3 wt. %, based on the total weight of the aqueous media. In some particular embodiments an alkali metal salt is present in the aqueous media at a level of between about 0.01 wt. % and about 4 wt. % or at a level of between about 0.01 wt. % and about 3.5 wt. %, based on the total weight of the aqueous media. A hexaalkylguanidinium salt may undergo some dealkylation to form the corresponding pentaalkylguanidine, for example under displacement reaction conditions. Thus, in another embodiment an aqueous medium comprises a first guanidinium salt and one or both of a neutral guanidine compound and its corresponding protonated analog (that is, a second guanidinium compound which is the protonated decomposition product a first guanidinium compound). In another particular embodiment an aqueous medium comprises hexaethylguanidinium chloride and one or both of pentaethylguanidine and pentaethylguanidinium chloride (the protonated decomposition product of hexaethylguanidinium chloride).

In other embodiments displacement reaction mixtures may optionally comprise still other inorganic or organic components in addition to at least one guanidine compound. Washing said reaction mixture with water may result in an aqueous medium comprising at least one guanidine compound and additional components which may be at least partially water-soluble. Said additional inorganic or organic components may be removed along with a guanidine compound from aqueous media by methods of the present invention. Therefore, it is to be understood that, although removal of a guanidine compound is referred to, additional organic or inorganic components may also be present in the aqueous media and may also be removed using the teachings herein. In a particular embodiment an aqueous medium may optionally comprise an imidization catalyst used in a displacement reaction. Suitable imidization catalysts are known in the art; they include salts of organophosphorus acids, particularly phosphinates such as sodium phenylphosphinate and heterocyclic amines such as 4-diaminopyridine. A preferred catalyst is sodium phenylphosphinate also known as phenyl phosphinic acid, sodium salt. Imidization catalyst levels in the aqueous media can vary widely, for example from about 10 ppm to about 5000 ppm. In another particular embodiment an aqueous medium may optionally comprise an organic component of a polymerization reaction, such as a monomer or end-capping agent or a reaction product thereof. In an illustrative example chlorophthalic acid may be present in aqueous media obtained by washing a polymerization reaction mixture used to prepare a polyetherimide. Chlorophthalic acid levels in the aqueous media can vary widely, for example from about 1 ppm to about 20,000 ppm. In some particular embodiments chlorophthalic acid levels in the aqueous media can vary from about 1 ppm to about 5,000 ppm, or from about 1 ppm to about 2,000 ppm.

In one embodiment of the invention aqueous media is contacted with a carbon adsorbent to remove a guanidine compound. Suitable carbon adsorbents may be activated carbons. Activated carbons can be produced by pyrolyzing organic materials such as coal, peat, or coconut shells under high temperatures in a nonoxidizing environment. The raw carbonaceous material can also be mixed with a binding agent to form a granular material. The pyrolyzed carbonaceous material can then be activated by steaming to create a high capacity, high surface area adsorbent. Raw materials with low metals content are sometimes preferred as they produce more pure activated carbons with a final lower metals content although an acid wash step can be used leach some of the residual metals from the as produced activated carbon. In many embodiments the carbon is acid washed to prevent leaching of components from the adsorbent into an acidic solution to be treated. One suitable activated carbon material that is commercially available is Type CPG Granular Carbon with particle size between 12 mesh and 40 mesh (i.e. mesh size 12×40), available from Calgon Carbon Corporation. Other factors useful in selecting activated carbons include base exchange capacity and particle size. Optimum activated carbons for treating a particular guanidine compound-comprising aqueous media may be determined without undue experimentation by those skilled in the art.

In another embodiment of the invention a suitable carbon adsorbent may be derived from the pyrolysis of a synthetic resinous polymer. Sometimes referred to as hard carbon adsorbents, such adsorbents and their method of preparation are described, for example, in U.S. Pat. Nos. 4,040,990 and 4,957,897. As described therein, these carbons are partially pyrolyzed particles preferably in the form of hard beads or spheres and having multimodal pore size, including micro and macro pores. They are produced by the controlled decomposition of a synthetic polymer. The pyrolysis, as described in U.S. Pat. No. 4,040,990, is generally conducted in an inert atmosphere comprised of, for example, helium, argon, or nitrogen. Any of the many synthetic polymers disclosed in U.S. Pat. No. 4,040,990 can be employed in preparing the hard carbon adsorbent for the process of this invention. In some embodiments suitable polymers are those derived from aliphatic and aromatic materials which are ethylenically unsaturated. In other embodiments the polymer is cross-linked, because cross-linking often stabilizes the polymer thermally and leads to greater carbon yields. In still other embodiments the polymer contains a carbon-fixing moiety, such as a cation, anion, strong base, weak base, sulfonic acid, carboxylic acid, halogen, or alkylamine moiety. Particular examples of suitable polymers include polyvinylidene chloride, and macroreticular ion-exchange resins derived from aliphatic and aromatic materials which are ethylenically unsaturated. In one particular embodiment the synthetic polymer is a polystyrene-divinylbenzene sulfonic acid ion-exchange resin. In addition to the polymers disclosed above, any of the polysulfonated polymers disclosed in U.S. Pat. No. 4,839,331 can be employed in preparing a hard carbon adsorbent for processes of the invention. Suitable hard carbon adsorbents include, but are not limited to, those commercially available under the name AMBERSORB, available from Rohm and Haas Co.

Typically the hard carbon adsorbents are highly stable, chemically, thermally and physically. In general they have a surface area of about 100-2000 $m^2/g$, usually about 500-1200 $m^2/g$ and can be used, for example, in the form of approximately spherical particles having a mean particle size of, for example, from about 0.2 to 1.5 mm, preferably from about 0.3 to 1.0 mm.

In particular embodiments hard carbon adsorbents, which are prepared by the pyrolysis of a synthetic resinous polymer, typically contain at least three distinct sets of pores of differing average size. One set comprises large pores or macropores, which typically range in size of at least 500 Angstroms in average diameter. The second set comprises intermediate pores or mesopores, which typically range in size from about 20 Angstroms to about 500 Angstroms. The third set and smallest pores or micropores are typically less than about 20 Angstroms in average diameter; however, the exact size depends on the temperature of pyrolysis of the synthetic polymer. In addition to pore size, the pyrolysis temperature also controls total pore volumes. Generally, as the pyrolysis temperature increases, the micropore volume increases.

The macropore volume of hard carbon adsorbents useful for this invention are typically at least 0.10 ml/g; preferably in the range from about 0.10 ml/g to about 0.35 ml/g; more preferably in the range from about 0.15 ml/g to about 0.30 ml/g; and most preferably in the range from about 0.20 ml/g to about 0.25 ml/g. The mesopore volume of hard carbon adsorbents useful for this invention are typically in the range from about 0.05 ml/g to about 0.30 ml/g; preferably in the range from about 0.10 ml/g to about 0.25 ml/g; and most preferably in the range from about 0.12 ml/g to about 0.20 ml/g. The micropore volume of hard carbon adsorbents useful for this invention are at least about 0.10 ml/g; more preferably, in the range from about 0.20 ml/g to about 0.50 ml/g; and most preferably in the range from about 0.30 ml/g to about 0.45 ml/g.

The process for removal of a guanidine compound from aqueous media using a carbonaceous adsorbent (either activated carbon or hard carbon adsorbent) can be implemented in accordance with conventional methods for adsorption processes, for example as illustrated in U.S. Pat. Nos. 5,094,754 and 5,104,530. In some particular embodiments said process comprises bringing said aqueous media into contact with said carbonaceous adsorbent for a time sufficient to allow a guanidine compound to be adsorbed from said aqueous media onto said carbonaceous adsorbent; and separating said aqueous media from said carbonaceous adsorbent containing said absorbed guanidine compound. In some embodiments the carbonaceous adsorbents may be used in the form of a slurry or contained in a column or filter bed. The optimum particle size of the carbon may depend upon such factors as the particular mode of operation, e.g. slurrying the carbon with the aqueous media or passing the aqueous media through a column of activated carbon., and may be determined without undue experimentation by those skilled in the art. When in the form of a column or filter bed, the carbonaceous adsorbent bed may operated in an up flow process or a down flow process. In other embodiments two or more carbonaceous adsorbent beds may be connected in series. The process for removal of a guanidine compound from aqueous media using a carbonaceous adsorbent may be operated in continuous, semi-continuous or batch mode.

When a carbon adsorbent is used to remove at least one guanidine compound from aqueous media, then the pH of the aqueous media may be in any convenient range, typically between about 1 and about 13. In some particular embodiments the pH of the aqueous media is greater than about 7. In other particular embodiments the pH of the aqueous media is in a range of between about 8 and about 13 or in a range of between about 9 and about 11.

In another embodiment of the invention aqueous media is contacted with a clay adsorbent to remove a guanidine compound. Suitable clays typically comprise layered clays, usually silicate clays. There is no particular limitation with respect to the layered clays that may be employed in this invention other than that they are capable of decreasing the concentration of guanidine compounds in an aqueous media. Illustrative of such layered clays that may be employed in this invention include, for instance, smectite and those of the kaolinite group such as kaolinite, halloysite, dickite, nacrite and the like.

The layered clays are preferably natural or synthetic phyllosilicates, particularly smectic clays. Illustrative examples include, for instance, halloysite, montmorillonite, nontronite, beidellite, saponite, volkonskoite, laponite, sauconite, magadite, kenyaite, bentonite, stevensite, and the like. It is also within the scope of the invention to employ clays comprising minerals of the illite group, including hydromicas, phengite, brammallite, glaucomite, celadonite and the like. Often, the preferred layered minerals include those often referred to as 2:1 layered silicate minerals, including muscovite, vermiculite, saponite, hectorite and montmorillonite, the latter often being most preferred. The clays may be synthetically produced, but most often they comprise naturally occurring minerals and are commercially available. Mixtures containing at least one of the clays as described herein are also suitable. Other suitable clay adsorbents include those described in U.S. Pat. No. 5,530,052. Preferred layered clays comprise particles containing a plurality of silicate platelets having a thickness of about 7-15 angstroms bound together at interlayer spacings of about 4 angstroms or less, and containing exchangeable cations such as $Na^+$, $Ca^{+2}$, $K^+$, $Al^{+3}$, and/or $Mg^{+2}$ present at the interlayer surfaces. The clays typically have a cation exchange capacity of about 50-200 milliequivalents per 100 grams on a dry basis. In various embodiments of the invention the clay adsorbents are employed when predominantly in their alkali metal ion forms and particularly in their sodium ion forms. Generally, the clays are swollen with an aqueous solution prior to use to increase their adsorption capacity.

The process for removal of a guanidine compound from aqueous media using a clay adsorbent can be implemented in accordance with conventional methods for adsorption processes. In some particular embodiments said process comprises bringing said aqueous media into contact with said clay adsorbent for a time sufficient to allow a guanidine compound to be adsorbed from said aqueous media onto said clay adsorbent; and separating said aqueous media from said clay adsorbent containing said absorbed guanidine compound. Illustrative methods of contacting the clay with the aqueous media comprising at least one guanidine compound include flow through columns and batch methods. The column method involves passing the aqueous media through a packed column of clay. Another method is to contact the clay with the aqueous media in a fluidized bed manner, for example an upflow of the aqueous media through a bed of clay. Additionally, stirred beds of clay may be contacted with the aqueous media. In a batch method of contacting the clay with the aqueous media, the clay is added to the aqueous media as a finely divided powder and after a sufficient amount of time is removed by well-known methods, illustrative examples of which comprise filtration, flocculation, flotation or centrifugation. In this mode of operation, the guanidine compound is sorbed on the clay and removed from the aqueous media when the clay is physically removed.

In yet another embodiment of the invention aqueous media is contacted with a nanofiltration membrane to remove a guanidine compound. Nanofiltration is a known operation in which a solution or dispersion of a material to be treated is passed over a nanofiltration separation membrane at a pressure which is generally in the range of from about 1 to about 5 megapascals (depending upon the strength of the membrane) to cause the lower molecular weight materials to pass through the membrane along with the water to form a permeate and an aqueous phase which does not pass through the membrane, which is known as a retentate. An increase in pressure usually increases the rate of permeate formation. However, the pressure which can be utilized may be determined by such factors as the temperature, nature of the particular nanofiltration membrane and the particular design of the nanofiltration apparatus and may be readily determined without undue experimentation by those skilled in the art.

Upon passage through the nanofiltration module, the permeate has a lower concentration of the guanidine compound than the retentate or the initial aqueous media.

A suitable nanofiltration membrane has a molecular weight cut-off (MWCO) which is often related to membrane pore size, and which retains the guanidine compounds while allowing water to pass through the membrane. The desired MWCO is generally less than the molecular weight of a guanidine compound in the aqueous media. Nanofiltration membranes generally have a nominal MWCO of between about 100 Daltons (Da) and about 5 kilodaltons (kDa), or between about 100 Da and about 3 kDa, or between about 100 Da and about 1 kDa, or between about 100 Da and about 600 Da, or between about 150 Da and about 600 Da. In some embodiments a suitable nanofiltration membrane has an MWCO sufficient to retain from about 40% to about 100% of the guanidine compound, preferably from about 70% to about 100% of the guanidine compound, and more preferably from about 80% to about 100% of the guanidine compound. The process for removal of a guanidine compound from aqueous media using a nanofiltration membrane may be operated in continuous, semi-continuous or batch mode.

Suitable nanofiltration membranes comprise sintered metal, ceramics or polymeric materials. Suitable polymeric nanofiltration membranes may be made, for example, of cellulose, cellulose acetate, polyamide, aramid, polyether, polysulfone, polyethersulfone, polyvinylpyrrolidone, polytetrafluoroethylene, or polyvinylidene fluoride; and are commercially available from several manufacturers, including Desalination Membrane Products (Escondido, Calif.), Dow/Film Tec Corporation (Minneapolis, Minn.), Osmonics (Minnetonka, Minn.), and Membrane Products Kiryat Weizman Ltd. (Rehovot, Israel). The type of membrane which is selected may be dependent upon such factors as the pH of the aqueous media to be treated with the nanofiltration unit, the molecular weight cut-off required, and the temperature and pressure at which the nanofiltration is to be carried out.

In yet another embodiment of the invention aqueous media is subjected to removal of water and calcination to remove a guanidine compound. Water may be removed from the aqueous media by any convenient method. In a particular embodiment water is removed by evaporation. Evaporation may be conducted at any convenient pressure, typically at or below atmospheric pressure. Removal of water typically leaves less than 5 wt. % of the original amount of water remaining. Following removal of water the substantially solid residue is subjected to calcination at a temperature of greater than 400° C. or greater than 450° C. or greater than 500° C. In one embodiment calcination is performed at a temperature in a range of between about 500° C. and about 600° C. The time of calcination is typically such that substantially all organic residue comprising a guanidine compound is burned off. Removal of substantially all organic residue typically leaves less than 5 wt. % of the original organic residue remaining. In a particular embodiment removal of substantially all organic residue typically leaves less than 5 wt. % or less than 2 wt. % of the initial amount of guanidine compound, based on the weight of guanidine compound initially present in aqueous media. In some particular embodiments removal of substantially all organic residue results in no detectable guanidine compound remaining, and less than 1000 ppm, or less than 500 ppm, or less than 200 ppm total organic carbon remaining. There are no particular limitations on the apparatus or protocol for performing calcination. Calcination may be performed under air or under an inert atmosphere. Removal of water and calcination may be performed in continuous, semi-continuous or batch mode. Following calcination any solid residue may be disposed of in an appropriate manner such as land-filling.

Following treatment of aqueous media to remove a guanidine compound using the method of the invention the concentration of guanidine compound in aqueous media is less than 50% of the initial concentration, or less than 30% of the initial concentration, or less than 25% of the initial concentration, or less than 20% of the initial concentration, or less than 15% of the initial concentration, or less than 10% of the initial concentration. In the case of an aqueous medium treated using a nanofiltration membrane the final concentrations of guanidine compound refer to that part of the aqueous medium which has passed through the membrane. In the case of an aqueous medium treated by removal of water and calcination of the residue, the final concentrations of guanidine compound refers to weight percent based on the weight initially present in the aqueous medium. If so desired, more than one step or a combination of steps selected from the group consisting of adsorption onto a carbonaceous adsorbent, adsorption onto a clay adsorbent, filtration through a nanofiltration membrane, and removal of water and calcination may be employed for removal of a guanidine compound from aqueous media.

Furthermore, following treatment of aqueous media to remove a guanidine compound, an additional inorganic or organic component which may optionally be present and which may be concurrently removed by methods of the present invention along with the guanidine compound may remain at a concentration in aqueous media of less than 50% of its initial concentration, or less than 30% of its initial concentration, or less than 25% of its initial concentration, or less than 20% of its initial concentration, or less than 15% of its initial concentration, or less than 10% of its initial concentration, depending upon such factors as the identity of the additional component, the type of treatment method, and the amount of adsorption agent.

In some embodiments of the invention a guanidine compound may optionally be recovered from the adsorption media. Any known means may be used for recovery. In some embodiments a guanidine compound may be at least partially recovered from a carbonaceous adsorbent by treating the adsorbent with a boiling aqueous solution. Optionally, a surfactant may be present in the aqueous solution to aid in recovery of the guanidine compound. In other embodiments a guanidine compound may be at least partially recovered from a carbonaceous or clay adsorbent by treating the adsorbent with an acidic media, particularly an aqueous acidic solution, optionally at elevated temperature and optionally containing a surfactant. Acidic solutions may be derived from either organic or inorganic acids.

In yet another embodiment a guanidine compound may be recovered from an aqueous media in which the guanidine compound has previously been concentrated through contact of the aqueous media with a nanofiltration membrane. Illustrative methods for recovering a guanidine compound from aqueous media include removal of water or adsorption of the guanidine compound on an adsorbent. Recovered guanidine compounds may be recycled and reused in chemical processes, illustrative examples of which include those described herein above. If necessary, a guanidine compound may be reactivated before reuse, such as by neutralization in the case of a protonated guanidine compound or by alkylation in the case of a dealkylated guanidine compound or by ion exchange in the case of a guanidinium compound. The carbonaceous and clay adsorbents and the nanofiltration membranes themselves may optionally be regenerated and optionally reused.

Although the invention is illustrated by treatment of wastewater comprising at least one guanidine compound and optionally additional inorganic or organic components which may be at least partially water-soluble, it is to be understood that the method of the invention is also applicable for treatment of wastewater comprising said inorganic or organic components in the absence of at least one guanidine compound. In particular embodiments the method of the invention may be used to remove an imidization catalyst such as sodium phenylphosphinate or an organic component of a polymerization reaction, such as a monomer or end-capping agent or a reaction product thereof, illustrative examples of which include chlorophthalic acid. In other particular embodiments the method of the invention may be used to remove both an imidization catalyst such as sodium phenylphosphinate and an organic component of a polymerization reaction, such as a monomer or end-capping agent or a reaction product thereof, illustrative examples of which include chlorophthalic acid.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner. In the following examples HEGCl is an abbreviation for hexaethylguanidinium chloride and PEG is an abbreviation for pentaethylguanidine.

EXAMPLE 1

In the following examples Calgon CPG acid-washed granular carbon was pulverized using a cryo-grinder. The pulverized carbon was sieved and particles of less than 325 mesh were collected and dried at 150° C. for 4 hours for use in isotherm experiments. Said carbon is referred to hereinafter as sieved Calgon CPG carbon. Unless adjusted by the addition of acid or base, the pH of the wastewater samples was generally in a range of between about 3 and 5.

A wastewater sample comprised 3.2 wt. % sodium chloride, 348 miligrams per liter (mg/L) of HEGCl and 72 mg/L of PEG. Six wastewater samples (10 milliliters (ml) each) were individually treated with 50 mg. sieved Calgon CPG carbon and agitated for various periods of time at room temperature in a mechanical shaker. The samples were filtered and the filtrates were analyzed for concentration of HEGCl and PEG versus time. Values are given in Table 1. The data show the equilibrium is reach very quickly (less than about 5 minutes).

TABLE 1

| Time (minutes) | conc. HEGCl (mg/ml) | conc. PEG (mg/ml) |
| --- | --- | --- |
| 0 | 0.35 | 0.07 |
| 5 | 0.04 | 0.01 |
| 10 | 0.04 | 0.01 |
| 30 | 0.04 | 0.01 |
| 60 | 0.05 | 0.01 |
| 90 | 0.04 | 0.01 |

EXAMPLE 2

For determination of adsorption isotherms sieved Calgon CPG carbon was dried at 150° C. for 4 hours and then added in varying amounts in grams per liter (g/L) to wastewater samples as described in Example 1. The samples were agitated for 15 minutes at room temperature in a mechanical shaker. The samples were filtered and the filtrates were analyzed to provide amount of HEGCl and PEG adsorbed per unit weight of adsorbent versus concentration of adsorbent in the mixture. Values are given tn Table 2.

Some conclusions may be drawn from the data in Table 2. From linear extrapolation the adsorptive capacity of the carbon adsorbent was found to be approximately 78 mg. HEGCl per gram Calgon CPG adsorbent when equilibrium had been established under the specified conditions. Somewhere between about 65 mg. and about 100 mg. of carbon removed essentially all traces of HEGCl and PEG from 10 ml. of wastewater containing these particular concentrations of wastewater components.

TABLE 2

| Wt. of carbon (g/L) | Concentration of HEGCl in solution (mg/L) | mg. HEGCl adsorbed | mg. HEGCl adsorbed per gram of carbon | Concentration of PEG in solution (mg/L) | mg. PEG adsorbed | mg. PEG adsorbed per gram of carbon |
| --- | --- | --- | --- | --- | --- | --- |
| 0 | 347.7 | — | — | 72 | — | — |
| 0.51 | 303.5 | 44.2 | 86.7 | 65.4 | 6.6 | 12.9 |
| 1.01 | 280.2 | 67.5 | 66.8 | 59.7 | 12.3 | 12.2 |
| 2.05 | 200 | 147.7 | 72.0 | 40.7 | 31.3 | 15.2 |
| 3.54 | 107.54 | 240.2 | 67.8 | 21.4 | 50.6 | 14.3 |
| 5.03 | 55.2 | 292.5 | 58.2 | 11.5 | 60.5 | 12.0 |
| 6.54 | 15 | 332.7 | 50.9 | 3.8 | 68.2 | 10.4 |
| 10.03 | 0 | 347.7 | 34.7 | 0 | 72 | 7.2 |
| 24.93 | 0 | 347.7 | 13.9 | 0 | 72 | 2.9 |
| 50.1 | 0 | 347.7 | 6.9 | 0 | 72 | 1.4 |
| 100 | 0 | 347.7 | 3.5 | 0 | 72 | 0.7 |

EXAMPLE 3

A wastewater sample comprised 3.2 wt. % sodium chloride, 237 miligrams per liter (mg/L) of HEGCl and 46 mg/L of PEG. Samples of the wastewater (10 ml. each) were treated with 50 mg. unpulverized Calgon CPG carbon. The pH of each mixture was adjusted to some value by the optional addition of either concentrated aqueous hydrochloric acid or 50% aqueous sodium hydroxide solution. Each mixture was agitated for 1 hour at room temperature in a mechanical shaker. The samples were filtered and the filtrates were analyzed for concentration of HEGCl and PEG. Values are given in Table 3. The data in Table 3 show that, as the pH is increased, the amounts of both ionic and neutral guanidine species adsorbed by the carbon adsorbent increases.

adsorbed by the carbon adsorbent increases, although the % increase diminishes at higher salt level.

TABLE 3

| pH | mg. HEGCl adsorbed per gram of carbon | mg. PEG adsorbed per gram of carbon |
|---|---|---|
| 1 | 40 | 9 |
| 3.5 | 46 | 10 |
| 13 | 62 | 14 |

TABLE 4

| Wt. % NaCl | mg. HEGCl adsorbed per gram of carbon | mg. PEG adsorbed per gram of carbon |
|---|---|---|
| 0 | 33 | 8 |
| 3.2 | 47 | 10 |
| 6.4 | 52 | 11 |

EXAMPLE 4

A wastewater sample comprised 237 miligrams per liter (mg/L) of HEGCl and 46 mg/L of PEG. Samples of the wastewater (10 ml. each) were treated with 50 mg unpulverized Calgon CPG carbon. Varying amounts of sodium chloride were dissolved in each mixture. Each mixture was agitated for 1 hour at room temperature in a mechanical shaker. The samples were filtered and the filtrates were analyzed for concentration of HEGCl and PEG. Values are given in Table 4. The data in Table 4 show that, as the polarity of the solution is increased through addition of increasing amounts of salt, the amounts of both ionic and neutral guanidine species

EXAMPLE 5

A wastewater sample with composition similar to that described above except comprising 6.4 wt. % sodium chloride was adjusted to pH 13 with 50% aqueous sodium hydroxide, treated with varying amounts of sieved Calgon CPG carbon and agitated for 1 hour at room temperature in a mechanical shaker. The sample was filtered and the filtrate was analyzed for concentration of HEGCl and PEG. Values are given in Table 5. From linear extrapolation the adsorptive capacity of the carbon adsorbent under these specified conditions was found to be approximately 139 mg HEGCl per gram of carbon adsorbent when equilibrium had been established.

TABLE 5

| Wt. of carbon (g/L) | Concentration of HEGCl in solution (mg/L) | mg. HEGCl adsorbed | mg. HEGCl adsorbed per gram of carbon | Concentration of PEG in solution (mg/L) | mg. PEG adsorbed | mg. PEG adsorbed per gram of carbon |
|---|---|---|---|---|---|---|
| 0 | 361 | — | — | 68 | — | — |
| 0.6 | 285 | 76 | 127 | 44 | 24 | 40 |
| 1.2 | 225 | 136 | 113 | 24 | 44 | 37 |
| 2.3 | 93 | 268 | 116 | 6 | 62 | 27 |
| 3.7 | 17 | 344 | 93 | 1 | 67 | 18 |
| 5.8 | 4 | 357 | 62 | 0 | 68 | 12 |

EXAMPLE 6

In the following examples AMBERSORB 572, a carbonaceous adsorbent with surface area of about 1100 square meters per gram ($m^2/g$), was obtained from Rohm and Haas in mesh size of 20-50, and was used as received. A wastewater sample comprised 3.2 wt. % sodium chloride, 348 mg/L of HEGCl and 78 mg/L of PEG. For determination of adsorption isotherms AMBERSORB 572 carbon was dried at 150° C. for 4 hours and then added in varying amounts in grams per liter (g/L) to individual wastewater samples as described in Example 1. The samples were agitated for 15 minutes at room temperature in a mechanical shaker. The samples were filtered and the filtrates were analyzed to provide amount of HEGCl and PEG adsorbed per unit weight of adsorbent versus concentration of adsorbent in the mixture. Values are given in Table 6.

Some conclusions may be drawn from the data in Table 6. From linear extrapolation the adsorptive capacity of the carbon adsorbent was found to be approximately 138 mg. HEGCl per gram of AMBERSORB 572 adsorbent when equilibrium had been established under the specified conditions. Somewhere between about 50 mg. and about 80 mg. of carbon removed essentially all traces of HEGCl and PEG from 10 ml. of wastewater containing these particular concentrations of wastewater components.

450 $m^2/g$; and AMBERLITE XAD-16 ("G") a non-ion-exchangeable adsorbent polymeric resin comprising structural units derived from styrene cross-linked with divinylbenzene and having a surface area of about 800 square meters per gram ($m^2/g$) and an average pore diameter of about 150 angstroms (Å).

TABLE 7

| Example | Adsorbent | mg/L HEGCl remaining | % HEGCl removed | mg/L PEG remaining | % PEG removed |
|---|---|---|---|---|---|
| Ex. 7 | A | 9 | 98 | 1 | 99 |
| Ex. 8 | B | 55 | 85 | 11 | 85 |
| C. Ex. 1 | C | 273 | 25 | 48 | 34 |
| C. Ex. 2 | D | 166 | 55 | 30 | 59 |
| C. Ex. 3 | E | 207 | 43 | 43 | 41 |
| C. Ex. 4 | F | 346 | 5 | 68 | 7 |
| C. Ex. 5 | G | 202 | 45 | 42 | 42 |

The data in Table 7 show that the non-ion-exchangeable adsorbent polymeric resins (Comparative Examples 2-5) have less capacity for adsorption of guanidine species than do

TABLE 6

| Wt. of carbon (g/L) | Concentration of HEGCl in solution (mg/L) | mg. HEGCl adsorbed | mg. HEGCl adsorbed per gram of carbon | Concentration of PEG in solution (mg/L) | mg. PEG adsorbed | mg. PEG adsorbed per gram of carbon |
|---|---|---|---|---|---|---|
| 0 | 366 | — | — | 73 | — | — |
| 0.5 | 281 | 85 | 170 | 49 | 24 | 48 |
| 0.9 | 248 | 118 | 131 | 41 | 32 | 35 |
| 2.1 | 165 | 201 | 96 | 23 | 50 | 23 |
| 3.4 | 83 | 283 | 83 | 7 | 66 | 19 |
| 5.7 | 6 | 360 | 63 | 0 | 73 | 12 |
| 7.8 | 0 | 366 | 47 | 0 | 73 | 9 |

EXAMPLES 7-8 AND COMPARATIVE EXAMPLES 1-5

Individual wastewater samples (30 ml. each) comprising 3.2 wt. % sodium chloride, 366 mg/L of HEGCl and 73 mg/L of PEG were stirred with 150 mg. of an adsorbent over 17 hours at ambient temperature. The samples were filtered and the filtrates were analyzed for amount of HEGCl and PEG in the mixture. Values are given in Table 7. Comparative Examples are designated "C.Ex.". The following adsorbents were used: AMBERSORB 572 ("A"); Calgon CPG ("B"); AMBERSORB 563 ("C"), a carbonaceous adsorbent with BET surface area of about 550 $m^2/g$ and about 62% of its pore volume associated with pores less than 2 nanometers (nm) and about 38% of its pore volume associated with pores of diameter greater than 2 nm and less than 30 nm.; AMBERLITE XAD-2 ("D") a non-ion-exchangeable adsorbent polymeric resin comprising structural units derived from styrene cross-linked with divinylbenzene; AMBERLITE XAD-4 ("E") a non-ion-exchangeable adsorbent polymeric resin comprising structural units derived from styrene cross-linked with divinylbenzene and having a surface area of about 750 $m^2/g$ and an average pore diameter of about 100 angstroms (Å); AMBERLITE XAD-7 ("F") a non-ion-exchangeable adsorbent polymeric resin having methyl methacrylate units rather than styrene units and having a surface area of about the carbonaceous adsorbents of Examples 7 and 8. In comparing Example 7 with Comparative Example 1 it is evident that the carbonaceous adsorbent with the higher surface area has a higher capacity for adsorption of guanidine species.

EXAMPLE 9

An aqueous solution comprising HEGCl and PEG was subjected to filtration through a nanofiltration membrane comprising polytetrafluoroethylene (Osmonics type DK-5). The membrane pore size was such that it rejects 98% magnesium sulfate. The experimental protocol employed a standard membrane test cell (SEPA-CF test apparatus) in which wastewater at pH 1 was pumped in a crossflow manner across the surface of the membrane in a continuous fashion at a pressure of 276-310 kilopascals and flow rate of 2 liters per minute with 2 hour cycle time. Permeate flux was measured volumetrically and HEGCl/PEG concentrations in permeate and retentate were measured via ion chromatography. Data are shown in Table 8. The difference between "Feed" amount and the sum of "Retentate" and Permeate" represents experimental error. The data show that the concentration of guanidine species in the permeate is approximately 7-8 times lower than the initial concentration of said species in the feed.

TABLE 8

| Sample | Amount (grams) | HEGCl (ppm) | PEG (ppm) |
|---|---|---|---|
| Feed | 332 | 3021 | 931 |
| Retentate | 195 | 4300 | 1345 |
| Permeate | 149 | 384 | 120 |

EXAMPLES 10-18

Sodium montmorillonite (type KUNIPIA-F; sometimes referred to herein after as "clay") was obtained from Kunimine Industries, Japan, and had a cation exchange capacity of 119 milliequivalents of sodium per 100 grams of clay on a basis of 90% dry weight of clay. Simulated wastewater solutions were prepared by dissolving various amounts of HEGCl in deionized water. Varying equivalent amounts of sodium montmorillonite were suspended in water in a high-speed blender and the HEGCl solution was added thereto under various conditions with agitation at room temperature. The mixtures were filtered and the filtrates were analyzed by ion chromatography for amount of HEGCl remaining. Values are given in Table 9. The abbreviation "equiv." means "equivalents". The column for "Conditions" includes the time of agitation.

TABLE 9

| Example | Concentration of HEGCl initially (mg/L) | Concentration of HEGCl remaining (mg/L) | % HEGCl removal | Conditions |
|---|---|---|---|---|
| 10 | 606 | 175 | 71 | 1 equiv. clay; 10 min. |
| 11 | 556 | 25 | 96 | 2 equiv. clay; 15 min. |
| 12 | 392 | 21 | 95 | 2 equivs. clay; 15 min.; clay mixture added to HEGCl soln. |
| 13 | 392 | 21 | 95 | Ex. 12 after 1 day aging |
| 14 | 392 | 19 | 95 | Ex. 12 after 4 days aging |
| 15 | 392 | 38 | 90 | 0.1 ml. HNO$_3$ added to 100 ml. soln. after agitation |
| 16 | 43 | 18 | 58 | 1 equiv. clay; 10 min. |
| 17 | 40 | 5 | 88 | 2 equiv. clay; 10 min. |
| 18 | 513 | 8 | 98 | 3 equiv. clay; 10 min. |

The data in Table 9 shows that greater than 1 equivalent of clay is necessary for efficient removal of HEGCl from solution under the conditions of the experiment. Little increase in HEGCl adsorption is obtained upon prolonged standing of the sample with clay (Examples 13-14).

EXAMPLES 19-22

Sodium montmorillonite was used as in Examples 10-18. Individual wastewater samples comprising 366 mg/L of HEGCl; 73 mg/L of PEG and optionally 3.2 wt. % sodium chloride as noted were treated with 2 equivalents clay (based on HEGCl) and agitated under different conditions. The mixtures were filtered and the filtrates were analyzed by ion chromatography for amount of HEGCl and PEG remaining. Values are given in Table 10. The abbreviation "rt" means "room temperature".

TABLE 10

| Ex. | Conc. of HEGCl remaining (mg/L) | % HEGCl removal | Concentration of PEG remaining (mg/L) | % PEG removal | Conditions |
|---|---|---|---|---|---|
| 19 | 51 | 86 | 11 | 85 | 10 min. in blender at rt |
| 20 | 111 | 70 | 27 | 63 | 3.2 wt. % NaCl; shake overnight at rt |
| 21 | 154 | 58 | 29 | 60 | 3.2 wt. % NaCl in blender for 10 min. at rt |
| 22 | 100 | 73 | 36 | 51 | 3.2 wt. % NaCl in blender for 10 min. at 80° C. |

EXAMPLE 23

Wastewater samples comprised HEGCl, PEG and sodium phenylphosphinate (SPP). Samples of the wastewater (20 ml. each) were adjusted to either pH 1.9 or pH 13.9 with hydrochloric acid or aqueous sodium hydroxide, and treated with various amounts of pulverized Calgon CPG carbon. Each mixture was agitated for 1 hour at room temperature in a mechanical shaker. The samples were filtered and the filtrates were analyzed for concentration of HEGCl, PEG and SPP. Values are given in Table 11 ompared to the initial concentration of the measured components. The data in Table 11 show that, as the pH is increased, the amounts of both ionic and neutral guanidine species and of SPP adsorbed by the carbon adsorbent increases.

TABLE 11

| pH | Carbon weight, grams/20 ml. | HEGCl, ppm | PEG, ppm | SPP, ppm |
|---|---|---|---|---|
| 13.9 | 0 | 646 | 168 | 123 |
| 13.9 | 0.05 | 370 | 58 | 80 |
| 13.9 | 0.1 | 98 | 23 | 18 |
| 13.9 | 0.15 | 54 | 18 | 18 |
| 13.9 | 0.2 | 0 | 17 | 7 |
| 13.9 | 0.25 | 0 | 0 | 3 |
| 1.9 | 0 | 675 | 169 | 116 |
| 1.9 | 0.05 | — | — | 85 |
| 1.9 | 0.1 | 512 | 92 | 53 |
| 1.9 | 0.15 | 96 | 21 | 22 |
| 1.9 | 0.2 | 71 | 17 | 16 |
| 1.9 | 0.25 | 31 | 4 | 4 |
| 1.9 | 0.3 | 0 | 0 | 2 |

EXAMPLE 24

In the following examples a reactivated Chemviron carbon (grade F400) was pulverized using a cryo-grinder. Individual wastewater samples (20 ml. each) comprising chlorophthalic acid (CIPA) were treated with various amounts of carbon at pH 4. Each mixture was agitated for 1.5 hour at room temperature in a mechanical shaker. The samples were filtered and the filtrates were analyzed for concentration of CIPA.

Values are given in Table 12 compared to the initial concentration of the measured component.

TABLE 12

| Carbon weight, g/L | ClPA, mg/L |
|---|---|
| 0 | 1007 |
| 0.5 | 863 |
| 1.5 | 565 |
| 2.5 | 373 |
| 5 | 60 |
| 7.5 | 13 |
| 10 | 0 |
| 12.5 | 0 |
| 15 | 0 |

EXAMPLE 25

A 2.1 liter wastewater sample comprising 1000 ppm total HEGCl and PEG, 253 ppm SPP, and 2404 ppm total organic carbon was evaporated to dryness by distillation to yield 170 g residue and 1.8 liters distillate. Analysis of the distillate showed no detectable HEGCl, PEG, or SPP. A 70 g sample of solid residue was heated in a stationary furnace under flowing nitrogen at a heating rate of 50° C. per minute to a temperature of 600° C. and held at 600° C. for 6 hours. Analysis showed that the residue weighed 67.92 g and had 100 ppm total organic carbon with no detectable HEGCl, PEG, or SPP.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All Patents cited herein are incorporated herein by reference.

The invention claimed is:

1. A method for removing a neutral or an ionic guanidine compound from aqueous media comprising less than 4 wt. % of an alkali metal halide, wherein the method consists of filtration through a nanofiltration membrane wherein the nanofiltration membrane has a molecular weight cut-off sufficient to retain from about 70% to about 100% of the guanidine compound.

2. The method of claim 1, wherein the guanidine compound has the formula

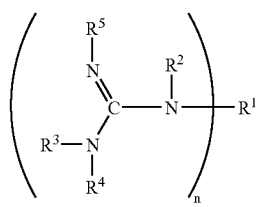

wherein each of $R^2$, $R^3$, $R^4$ and $R^5$ is independently a primary alkyl radical and $R^1$ is a primary alkyl or bis(primary alkylene) radical, or at least one of the $R^1$-$R^2$ or $R^3$-$R^4$ combinations with the connecting nitrogen atom forms a heterocyclic radical; and the value of the parameter n is 1 or 2.

3. The method of claim 1, wherein the guanidine compound has the formula

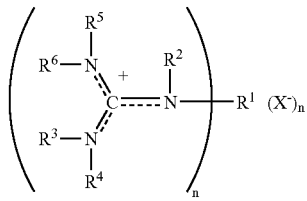

wherein each of $R^2$, $R^3$, $R^4$, $R^5$ and $R^6$ is independently a primary alkyl radical and $R^1$ a primary alkyl or bis(primary alkylene) radical, or at least one of $R^2$, $R^3$, $R^4$, $R^5$ and $R^6$ is hydrogen, or at least one of the $R^1$-$R^2$, $R^3$-$R^4$ or $R^5$-$R^6$ combinations with the connecting nitrogen atom forms a heterocyclic radical; the moiety X is an anion; and the value of the parameter n is 1 or 2.

4. The method of claim 1, wherein both a neutral and an ionic guanidine compound are removed from the aqueous media.

5. The method of claim 1, wherein the concentration of guanidine compound present initially in the aqueous media ranges from about 0.5 parts per million to about 100,000 parts per million.

6. The method of claim 1, wherein the aqueous media is free of alkali metal halide.

7. The method of claim 1, wherein the aqueous media comprises an alkali metal halide in an amount of between about 0.01 wt. % and about 4 wt. %.

8. The method of claim 7, wherein the alkali metal halide is selected from the group consisting of sodium chloride and potassium chloride.

9. The method of claim 1, wherein the concentration of guanidine compound following removal is less than 30% of the initial concentration.

10. The method of claim 1, wherein the concentration of guanidine compound following removal is less than 15% of the initial concentration.

11. The method of claim 1, further comprising the step of recovering the guanidine compound.

12. The method of claim 1, wherein an additional inorganic or organic component is removed in addition to the neutral or ionic guanidine compound.

13. The method of claim 12, wherein the additional component is sodium phenylphosphinate.

14. The method of claim 13, wherein the additional component is chlorophthalic acid.

* * * * *